US00PP20068P2

(12) United States Plant Patent
Koning

(10) Patent No.: US PP20,068 P2
(45) Date of Patent: Jun. 9, 2009

(54) ***LAVENDER* PLANT NAMED 'SILVER ANOUK'**

(50) Latin Name: *Lavandula stoechas*
Varietal Denomination: Silver Anouk

(75) Inventor: Lammert Koning, TB Nuis (NL)

(73) Assignee: Koning Smit Holding B.V., Curacao (AN)

( * ) Notice: Subject to any disclaimer, the term of this patent is extended or adjusted under 35 U.S.C. 154(b) by 0 days.

(21) Appl. No.: 12/154,242

(22) Filed: May 21, 2008

(51) Int. Cl.
*A01H 5/00* (2006.01)

(52) U.S. Cl. ..... Plt./445
(58) Field of Classification Search ..... Plt./445
See application file for complete search history.

*Primary Examiner*—Annette H Para
(74) *Attorney, Agent, or Firm*—C. A. Whealy

(57) ABSTRACT

A new and distinct cultivar of *Lavender* plant named 'Silver Anouk', characterized by its compact and upright plant habit; freely branching growth habit; durable silvery green-colored leaves; freely flowering habit; large dark violet-colored flowers positioned on strong and erect peduncles; and good garden performance.

2 Drawing Sheets

Botanical designation: *Lavandula stoechas.*
Cultivar denomination: 'Silver Anouk'.

BACKGROUND OF THE INVENTION

The present invention relates to a new and distinct cultivar of *Lavender* plant, botanically known as *Lavandula stoechas,* and hereinafter referred to by the name 'Silver Anouk'.

The new *Lavender* is a naturally-occurring branch mutation of the *Lavandula stoechas* 'Anouk', disclosed in U.S. Plant Pat. No. 16,685. The new *Lavender* was discovered and selected by the Inventor on a single plant within a population of plants of 'Anouk' in a controlled outdoor nursery environment in Nuis, The Netherlands in June, 2006.

Asexual reproduction of the new *Lavender* by terminal cuttings in a controlled greenhouse environment in Sappemeer, The Netherlands since August, 2006, has shown that the unique features of this new *Lavender* are stable and reproduced true to type in successive generations.

SUMMARY OF THE INVENTION

Plants of the new *Lavender* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of the new *Lavender*. These characteristics in combination distinguish 'Silver Anouk' as a new and distinct cultivar of *Lavender*:

1. Compact and upright plant habit.
2. Freely branching growth habit.
3. Durable silvery green-colored leaves.
4. Freely flowering habit.
5. Large dark violet-colored flowers positioned on strong and erect peduncles.
6. Good garden performance.

Plants of the new *Lavender* differ from plants of the parent, 'Anouk', primarily in leaf color as plants of 'Anouk' have greyed green-colored leaves.

Plants of the new *Lavender* can be compared to plants of the *Lavender* 'Alexandra', not patented. In side-by-side comparisons conducted in Sappemeer, The Netherlands, plants of the new *Lavender* differed from plants of 'Alexandra' in the following characteristics:

1. Plants of the new *Lavender* had stronger and more durable stems than plants of 'Alexandra'.
2. Plants of the new *Lavender* and 'Alexandra' differed in leaf color as plants of 'Alexandra' had greyed green-colored leaves.
3. Plants of the new *Lavender* had shorter flower bracts than plants of 'Alexandra'.

BRIEF DESCRIPTION OF THE PHOTOGRAPHS

The accompanying photographs illustrate the overall appearance of the new *Lavender*. These photographs show the colors as true as it is reasonably possible to obtain in colored reproductions of this type. Colors in the photographs may differ slightly from the color values cited in the detailed botanical description which accurately describe the colors of the new *Lavender*.

The photograph on the first sheet comprises a side perspective view of a typical flowering plant of 'Silver Anouk' grown in a container.

The photograph at the top of the second sheet is a close-up view of typical inflorescence of 'Silver Anouk'.

The photograph at the bottom of the second sheet is a close-up view of a typical stems and leaves of 'Silver Anouk'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in 14-cm containers in Boskoop, The Netherlands during the spring in an outdoor nursery and under conditions and practices which approximate those generally used in commercial *Lavender* production. Measurements and numerical values represent averages for typical flowering plants. Plants were pinched two times and were one year old when the photographs and description were taken. During the production of the plants, day temperatures ranged from 4° C. to 20° C. and night temperatures ranged from 0° C. to 14° C.

Botanical classification: *Lavandula stoechas* 'Silver Anouk'.

Parentage: Naturally-occurring branch mutation of the *Lavandula stoechas* 'Anouk', disclosed in U.S. Plant Pat. No. 16,685.

Propagation:

*Type.*—Terminal vegetative cuttings.

*Time to initiate roots, summer.*—About two weeks at 14° C. to 25° C.

*Time to initiate roots, winter.*—About three weeks at 14° C. to 25° C.

*Time to produce a rooted young plant, summer.*—About eight weeks at 14° C. to 25° C.

*Time to produce a rooted young plant, winter.*—About ten weeks at 14° C. to 25° C.

*Root description.*—Fine, fibrous; white in color.

*Rooting habit.*—Freely branching; dense.

Plant description:

*Form.*—Herbaceous perennial. Compact and upright plant habit. Freely branching habit, about 29 lateral branches; moderately vigorous growth habit. Flowers in verticillasters on crowded spikes with showy terminal flower bracts.

*Plant height.*—About 34.2 cm.

*Plant width.*—About 31.9 cm.

*Lateral branch description.*—Length: About 17 cm. Diameter: About 2 mm. Internode length: About 3 mm. Strength: Strong. Aspect: Mostly upright. Texture: Densely tomentose. Color: Close to 144B; pubescence, close to 193C to 193D.

*Foliage description.*—Arrangement: Opposite, simple; sessile. Length: About 3.8 cm. Width: About 5 mm. Shape: Linear. Apex: Acute. Base: Cuneate. Margin: Entire. Texture, upper and lower surfaces: Densely tomentose. Fragrance: Very aromatic, pungent. Venation pattern: Pinnate. Color: Developing foliage, upper surface: Close to 191A to 191B. Developing foliage, lower surface: Close to 191D. Fully expanded foliage, upper surface: Close to 191A; venation, close to 191A; pubescence, close to 193C to 193D. Fully expanded foliage, lower surface: Close to 191B to 191C; venation, close to 191D; pubescence, close to 193C to 193D.

Flower description:

*Flower arrangement and shape.*—Small single flowers in compact verticillasters on crowded spikes. Freely flowering, about 170 open flowers and flower buds per spike; flowers tubular with five lobes; inflorescences with showy terminal bracts.

*Natural flowering season.*—Long flowering period; continuous throughout the summer in The Netherlands.

*Flower longevity on the plant.*—Individual inflorescences last about ten days on the plant. Flowers not persistent.

*Fragrance.*—Not detected.

*Flower buds.*—Length: About 4 mm. Diameter: About 2 mm. Shape: Obovate. Color: Close to 194A.

*Inflorescence size.*—Height: About 4.9 cm. Diameter, apex: About 2.6 cm. Diameter, base: About 1.5 cm.

*Flowers.*—Diameter: About 3.5 mm. Depth (height): About 7 mm.

*Petals.*—Arrangement: Five, fused into a tube. Length: About 7 mm. Width: About 1.5 mm. Shape: Roughly spatulate. Apex: Rounded. Margin: Entire. Texture, upper and lower surfaces: Smooth, glabrous. Color: When opening, upper and lower surfaces: Darker than N92B to N92C; tube, close to N88B to N88C. Fully opened, upper and lower surfaces: Darker than N92B to N92C; tube, close to N88B to N88C. With development, color becoming closer to darker than N92A.

*Terminal flower bracts.*—Quantity/arrangement: About four at inflorescence apex. Length: About 2.4 cm. Width: About 9 mm. Shape: Obovate. Apex: Obtuse to broadly acute. Base: Cuneate. Margin: Entire; wavy. Texture, upper and lower surfaces: Smooth, glabrous. Color, upper and lower surfaces: Close to 77B; midvein, close to 77A.

*Flower bracts.*—Arrangement: Each whorl of flowers subtended by a flower bract. Length: About 8 mm. Width: About 7 mm. Shape: Broadly rhomboidal. Apex: Broadly acute. Base: Cuneate. Margin: Entire. Texture, upper and lower surfaces: Densely tomentose. Color, upper and lower surfaces: Close to 186A; towards the base, close to 138A to 138B; venation, close to 147A.

*Calyx.*—Arrangement: Five sepals fused into a campanulate tube. Length: About 5 mm. Width: About 1.2 mm. Sepal shape: Lanceolate. Sepal apex: Acute. Sepal margin: Entire. Sepal texture, upper and lower surfaces: Densely tomentose. Color, upper and lower surfaces: Close to 145C to 145D; close to 193C to 193D.

*Peduncles.*—Strength: Strong. Length: About 8.7 cm. Diameter: About 2 mm. Aspect: Mostly upright. Texture: Densely pubescent. Color: Close to 144B; pubescence, close to 193C to 193D.

*Reproductive organs.*—Stamens: Quantity per flower: Four. Filament length: About 0.5 mm. Anther shape: Reniform. Anther length: About 0.5 mm. Anther color: Close to 165B. Pollen amount: Scarce. Pollen color: Close to 165B to 165C. Pistils: Quantity per flower: One. Pistil length: About 3.5 mm. Stigma shape: Club-shaped. Stigma color: Close to N186A. Style length: About 3 mm. Style color: Close to 155C. Ovary color: Close to 145D.

*Seed/fruit.*—Seed and fruit production has not been observed.

Disease/pest resistance: Plants of the new *Lavender* have not been noted to be resistant to pathogens and pests common to *Lavender*.

Garden performance: Plants of the new *Lavender* have exhibited good tolerance to rain and wind and have been observed to tolerate temperatures from 0° C. to 40° C.

It is claimed:

1. A new and distinct *Lavender* plant named 'Silver Anouk' as illustrated and described.

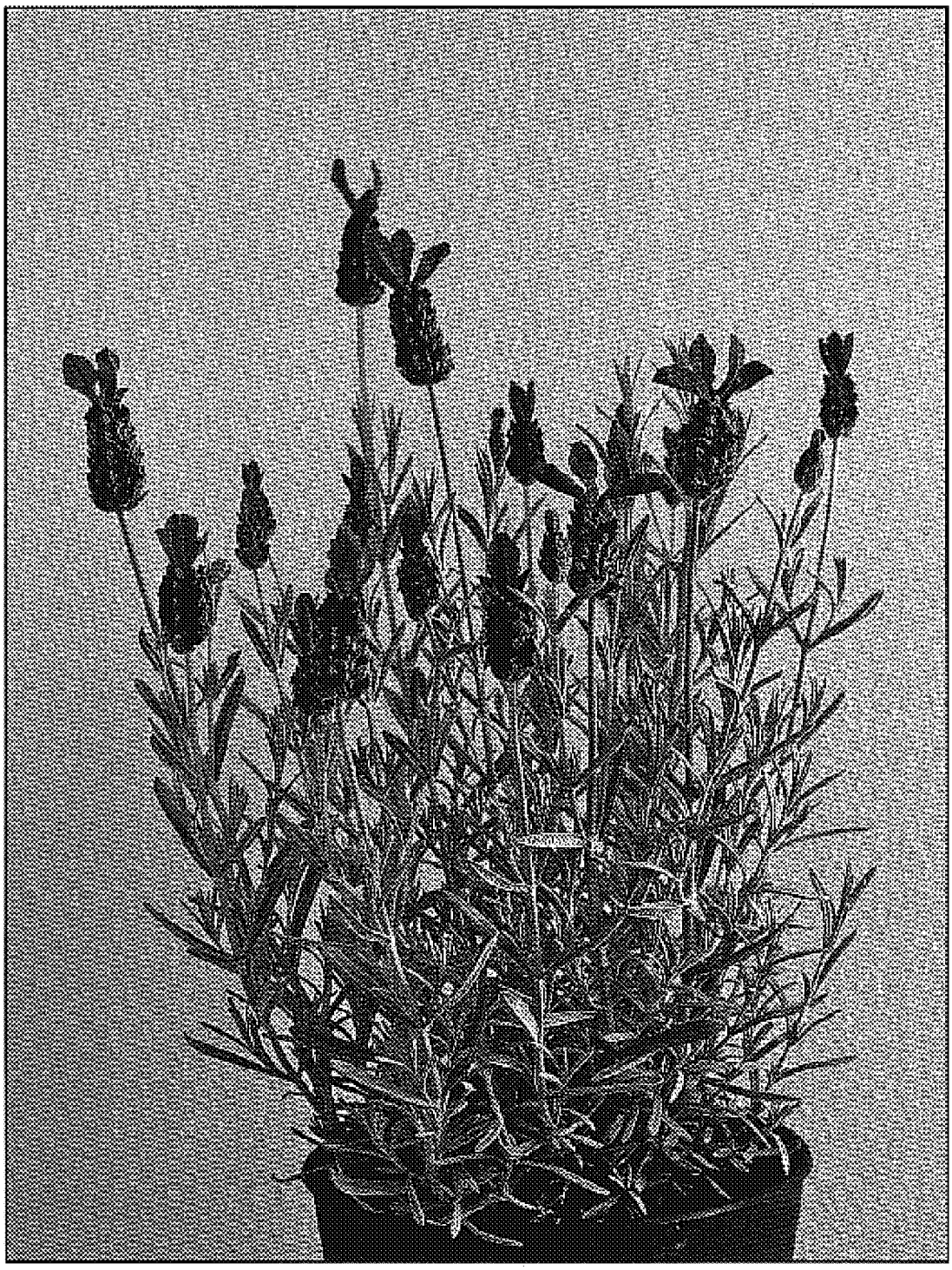

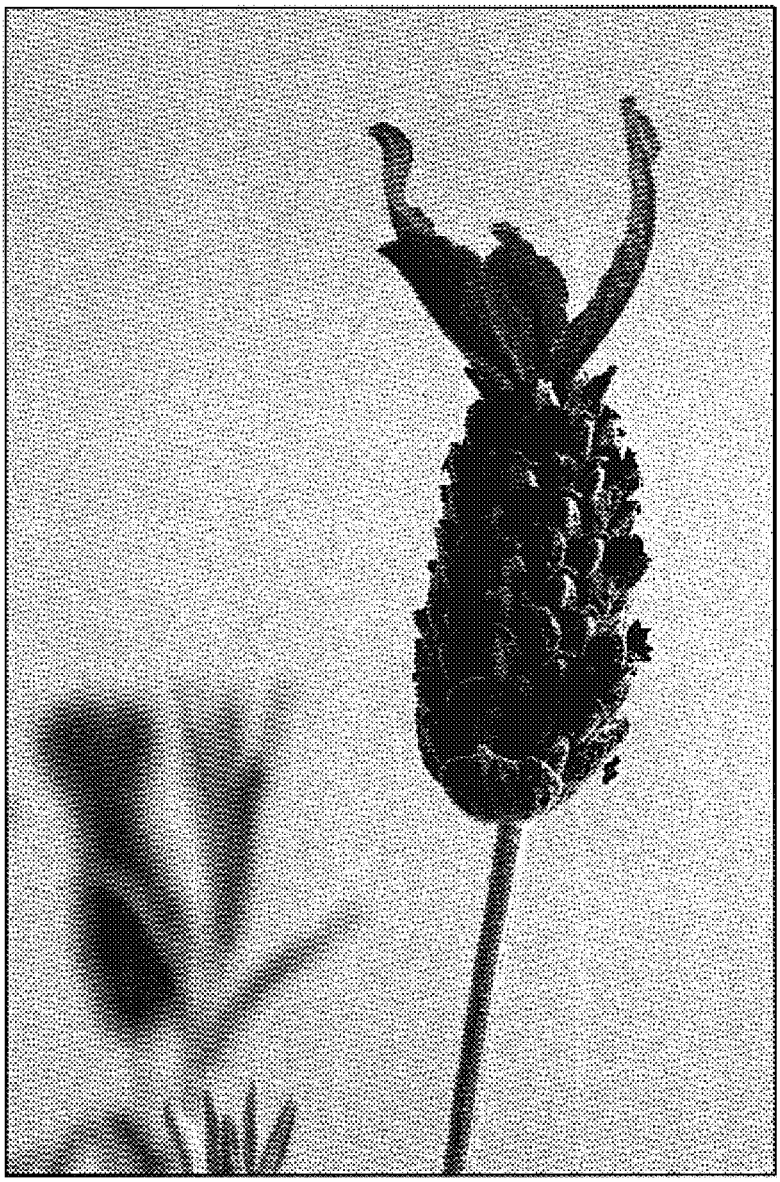
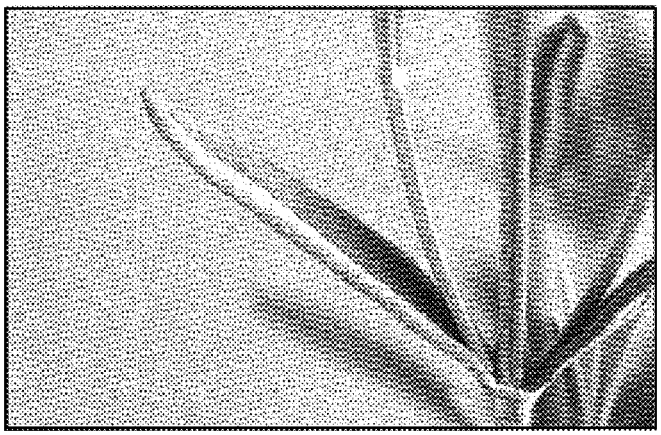

* * * * *